United States Patent
Wishart et al.

[11] Patent Number: 6,136,825
[45] Date of Patent: Oct. 24, 2000

[54] SULFONAMIDE COMPOUNDS HAVING 5-HT RECEPTOR ACTIVITY

[75] Inventors: Neil Wishart; Alan Martin Birch, both of Nottinghamshire, United Kingdom

[73] Assignee: Knoll Aktiengesellschaft

[21] Appl. No.: 09/331,066

[22] PCT Filed: Dec. 15, 1997

[86] PCT No.: PCT/EP97/07034

§ 371 Date: Jun. 16, 1999

§ 102(e) Date: Jun. 16, 1999

[87] PCT Pub. No.: WO98/29411

PCT Pub. Date: Jul. 9, 1998

[30] Foreign Application Priority Data

Dec. 27, 1996 [GB] United Kingdom ............... 9627006

[51] Int. Cl.[7] .................................. A01N 43/40
[52] U.S. Cl. ................... 514/321; 514/326; 546/193; 546/197
[58] Field of Search ................... 546/197, 193; 514/321, 326

[56] References Cited

U.S. PATENT DOCUMENTS

| | | | |
|---|---|---|---|
| 5,137,901 | 8/1992 | Junge et al. | 514/373 |
| 5,286,735 | 2/1994 | Bonnaud et al. | 514/321 |
| 5,300,523 | 4/1994 | Junge et al. | 514/456 |
| 5,506,246 | 4/1996 | Junge et al. | 514/373 |
| 5,585,392 | 12/1996 | Junge et al. | 514/373 |

FOREIGN PATENT DOCUMENTS

| | | |
|---|---|---|
| 352613 | 1/1990 | European Pat. Off. |
| 94/18193 | 8/1994 | WIPO |
| 95/07274 | 3/1995 | WIPO |

*Primary Examiner*—Amelia Owens
*Attorney, Agent, or Firm*—Keil & Weinkauf

[57] ABSTRACT

Compounds of formula (I) and pharmaceutically acceptable salts thereof in which A is methylene or —O—; B is methylene or —O—; g is 0, 1, 2, 3 or 4; U is an alkylene chain optionally substituted by one or more alkyl; Q represents a divalent group containing nitrogen atoms; and T represents an aryl or heteroaryl group, have utility in the treatment of central nervous system disorders, for example depression, anxiety, psychoses (for example schizophrenia), tardive dyskinesia, Parkinson's disease, obesity, hypertension, Tourette's syndrome, dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress and spasticity

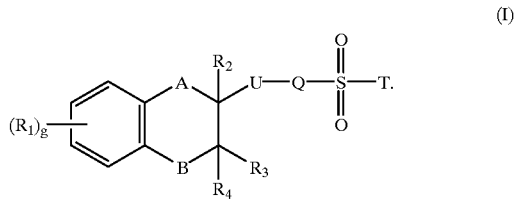

6 Claims, No Drawings

SULFONAMIDE COMPOUNDS HAVING 5-HT RECEPTOR ACTIVITY

The present invention relates to novel heteroarylsulphonamide compounds which have affinity for 5-HT$_{1A}$ and/or D$_2$-like (D$_2$, D$_3$ and D$_4$ sub-types) receptors, to processes for their preparation, to pharmaceutical compositions containing them and to their use in the treatment of central nervous system disorders, for example depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, and spasticity.

The present invention provides compounds of formula I

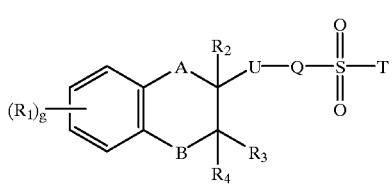

I including enantiomers and pharmaceutically acceptable salts thereof in which

A is methylene or —O—;

B is methylene or —O—;

g is 0, 1, 2, 3 or 4;

R$_1$ represents an alkyl group containing 1 to 3 carbon atoms optionally substituted by one or more halo; an alkoxy group containing 1 to 3 carbon atoms optionally substituted by one or more halo; halo; 6,7-methylenedioxy optionally C-substituted by one or two alkyl groups containing 1 to 3 carbon atoms; or an alkylthio group containing 1 to 3 carbon atoms optionally substituted by one or more halo; the substituents represented by R$_1$ being the same or different when g is 2, 3 or 4;

R$_2$ is H, an alkyl group containing 1 to 3 carbon atoms, or an alkoxy group containing 1 to 3 carbon atoms;

R$_3$ and R$_4$, which are the same or different, are H, or an alkyl group containing 1 to 3 carbon atoms;

U is an alkylene chain containing 1 to 3 carbon atoms, optionally substituted by one or more alkyl groups each containing 1 to 3 carbon atoms;

Q represents a divalent group of formula IIa, IIb or IIc

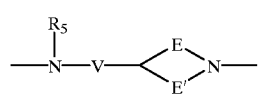

IIa

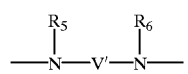

IIb

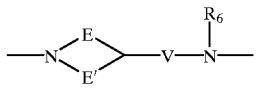

IIc in which V is the group (CH$_2$)n in which n is 0, 1, 2 or 3, optionally substituted by one or more alkyl groups each containing 1 to 3 carbon atoms;

V' is an alkylene chain containing 2 to 6 carbon atoms, optionally substituted by one or more alkyl groups each containing 1 to 3 carbon atoms;

E is an alkylene chain containing 0 to 2 carbon atoms and E' is an alkylene chain containing 1 to 4 carbon atoms provided that the total number of carbon atoms in E and E' amounts to 3 or 4;

R$_5$ and R$_6$, which may be the same or different, are H or an alkyl group containing 1 to 4 carbon atoms; and T represents phenyl, 1- or 2-naphthyl, 5-naphth[2,1-d][1,2,3]oxadiazolyl, 2-, 3- or 4-pyridyl, 2-, 4- or 5-pyrimidinyl, 2- or 3-thienyl, 2- or 3-furyl, 2-, 3- or 7-benzo[b]furanyl, 2,3-dihydro-7-benzo[b]furanyl, 2-, 3- or 7-benzo[b]thiophenyl, 3-, 4- or 5-pyrazol, 1,2,3-triazol-4-yl, 1,2,3-triazol-5-yl, 1,2,4-triazol-2-yl, 5-tetrazolyl, 2-, 3- or 4-quinolinyl, 2- or 4-quinazolinyl, 3-, 4- or 5-isoxazolyl, 2-, 4- or 5-oxazolyl, 3-, 4- or 5-isothiazolyl or 2-, 4- or 5-thiazolyl each of which may be optionally substituted by one or more substituents selected from a) halo, b) an alkyl group containing 1 to 4 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) hydroxy, f) an acyloxy group containing 1 to 3 carbon atoms, g) hydroxymethyl, h) cyano, i) an alkanoyl group containing 1 to 6 carbon atoms, j) an alkoxycarbonyl group containing 2 to 6 carbon atoms, k) a carbamoyl group or carbamoylmethyl group each optionally N-substituted by one or two alkyl groups each containing 1 to 3 carbon atoms, I) a sulphamoyl or sulphamoylmethyl group each optionally N-substituted by one or two alkyl groups each containing 1 to 3 carbon atoms, m) an amino group optionally substituted by one or two alkyl groups each containing 1 to 5 carbon atoms, n) 1-pyrrolidinyl or 1-piperidinyl, o) nitro or p) acetamido.

In preferred compounds of formula I, A is —O—.
In preferred compounds of formula I, B is —O—.
In more preferred compounds of formula I, both A and B are —O—.
In preferred compounds of formula I, g is 0 or 1. When g is 1, R$_1$ is preferably halo or an alkyl group containing 1 to 3 carbon atoms optionally substituted by one or more halo for example trifluoromethyl. In more preferred compounds of formula I, g is 1 and R$_1$ is halo. Most preferably g is 1 and R$_1$ is 7-chloro.
In preferred compounds of formula I, R$_2$ is H.
In preferred compounds of formula I, R$_3$ and R$_4$ are both H.
In preferred compounds of formula I, U is methylene.
In preferred compounds of formula I, Q is a group of formula IIc in which E and E' are both ethylene, V is methylene, and R$_6$ is H.
In preferred compounds of formula I, T represents phenyl, 1- or 2-naphthyl, 5-naphth[2,1-d][1,2,3]oxadiazolyl, or 2- or 3-pyridyl each of which may be optionally substituted by one or more substituents, which may be the same or different, selected from an alkyl group containing 1 to 3 carbon atoms optionally substituted by one or more halo, an alkoxy group containing 1 to 3 carbon atoms optionally substituted by one or more halo, nitro, acetamido, halo or an amino group optionally substituted by one or two alkyl groups each containing 1 to 3 carbon atoms.

In more preferred compounds of formula I, T represents phenyl, 1- or 2-naphthyl, 5-naphth[2,1-d][1,2,3]oxadiazolyl, or 2- or 3-pyridyl each of which may be optionally substituted by one or more substituents, which may be the same or different, selected from methyl, methoxy, trifluoromethyl, trifluoromethoxy, 2,2,2-trifluoroethoxy, nitro, acetamido, halo or an amino group optionally substitued by one or two alkyl groups each containing 1 to 3 carbon atoms.

In especially preferred compounds of formula I, T is 1-naphthyl, 2-naphthyl, 5-naphth[2,1-d][1,2,3]oxadiazolyl, 2-pyridyl, 3-pyridyl, phenyl, 4-methylphenyl, 2,4,6-trimethylphenyl, 2,3,4,5,6-pentamethylphenyl, 2-fluorophenyl, 4-fluorophenyl, 2,6-difluorophenyl, 2,4-difluorophenyl, 2,3,4-trifluorophenyl, 2-chlorophenyl, 4-chlorophenyl, 2,5-dibromophenyl, 4-iodophenyl, 2,5-dibromo-3,6-difluorophenyl, 4-methoxyphenyl, 2,5-dimethoxyphenyl, 3,4-dimethoxyphenyl, 4-methoxy-2,3,6-trimethylphenyl, 5-chloro-2-methoxyphenyl, 5-fluoro-2-methylphenyl, 4-trifluoromethoxyphenyl, 2,5-bis(2,2,2-trifluoroethoxy)phenyl, 3-trifluoromethylphenyl, 4-trifluoromethylphenyl, 2-chloro-4-trifluoromethylphenyl, 4-acetamidophenyl, 2-nitrophenyl, 3-nitrophenyl, 4-nitrophenyl, 2,4-dinitrophenyl, 4-methyl-3,5-dinitrophenyl, 5-(diethylamino)-1-naphthyl, 2,3-dichlorophenyl or 3-chloro-4-fluorophenyl.

In one group of preferred compounds of formula I, A is —O—, B is —O—, g is 1, $R_1$ is preferably halo or an alkyl group containing 1 to 3 carbon atoms optionally substituted by one or more halo, $R_2$ is H, $R_3$ and $R_4$ are both H, U is methylene, Q is a group of formula IIc in which E and E' are both ethylene, V is methylene, $R_6$ is H, and T is 1-naphthyl, 2-naphthyl, $^5$-naphth[2,1-d][1,2,3]oxadiazolyl, 2-pyridyl, 3-pyridyl, phenyl, 4-methylphenyl, 2,4,6-trimethylphenyl, 2,3,4,5,6-pentamethylphenyl, 2-fluorophenyl 4-fluorophenyl, 2,6-difluorophenyl, 2,4-difluorophenyl, 2,3,4-trifluorophenyl, 2-chlorophenyl, 4-chlorophenyl, 2,5-dibromophenyl, 4-iodophenyl, 2,5-dibromo-3,6-difluorophenyl, 4-methoxyphenyl, 2,5-dimethoxyphenyl, 3,4-dimethoxyphenyl, 4-methoxy-2,3,6-trimethylphenyl, 5-chloro-2-methoxyphenyl, 5-fluoro-2-methylphenyl, 4-trifluoromethoxyphenyl, 2,5-bis(2,2,2-trifluoroethoxy) phenyl, 3-trifluoromethylphenyl, 4-trifluoromethylphenyl, 2-chloro-4-trifluoromethylphenyl, 4-acetamidophenyl, 2-nitrophenyl, 3-nitrophenyl, 4-nitrophenyl, 2,4-dinitrophenyl, 4-methyl-3,5-dinitrophenyl, 5-(diethylamino)-1-naphthyl, 2,3-dichlorophenyl or 3-chloro-4-fluorophenyl.

Compounds of formula I may exist as salts with pharmaceutically acceptable acids. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. Compounds of formula I and their salts may exist in the form of solvates (for example hydrates).

It will be understood that any group mentioned herein which contains a chain of three or more atoms signifies a group in which the chain may be straight or branched. For example, an alkyl group may comprise propyl, which includes n-propyl and isopropyl, and butyl, which includes n-butyl, sec-butyl, isobutyl and tert-butyl. The term 'halo' as used herein signifies fluoro, chloro, bromo and iodo.

Compounds of formula I and intermediates in their preparation contain one or more chiral centres, and exist in different optically active forms. When compounds of formula I and intermediates in their preparation contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallisation; formation of diastereoisomeric derivatives or complexes which may be separated, for example, by crystallisation, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to this skilled in the art, for example chromatography or crystallisation and the individual enantiomers within each pair may be separated as described above. The present invention includes each diastereoisomer of compounds of formula I and mixtures thereof.

Certain compounds of formula I and their salts may exist in more than one crystal form and the present invention includes each crystal form and mixtures thereof. Certain compounds of formula I and their salts may also exist in the form of solvates, for example hydrates, and the present invention includes each solvate and mixtures thereof.

Specific compounds of formula I are:
N-{[1-(7-chloro-1,4-benzodioxan-2-ylmethyl)-4-piperidyl]methyl}pyridine-2-sulphonamide;
4-[N-(7-chloro-1,4-benzodioxan-2-ylmethyl)aminomethyl]-1-(2-pyridine-sulphonyl)piperidine;
N-{[1-(7-chloro-1,4-benzodioxan-2-ylmethyl)-4-piperidyl]methyl}pyridine-3-sulphonamide;
N-{[1-(7-chloro-1,4-benzodioxan-2-ylmethyl)-4-piperidyl]methyl}-4-nitrobenzene-sulphonamide;
N-{[1-(7-chloro-1,4-benzodioxan-2-ylmethyl)-4-piperidyl]methyl}-4-fluorobenzene-sulphonamide;
N-{[1-(7-chloro-1,4-benzodioxan-2-ylmethyl)-4-piperidyl]methyl}-3,4-dimethoxy-benzenesulphonamide;
N-{[1-(7-chloro-1,4-benzodioxan-2-ylmethyl)-4-piperidyl]methyl}-2,4-difluorobenzene-sulphonamide;
4-acetamido-N-{[1-(7-chloro-1,4-benzodioxan-2-ylmethyl)-4-piperidyl]methyl}-benzenesulphonamide;
N-{[1-(7-chloro-1,4-benzodioxan-2-ylmethyl)-4-piperidyl]methyl}-4-methoxybenzene-sulphonamide;
N-{[1-(7-chloro-1,4-benzodioxan-2-ylmethyl)-4-piperidyl]methyl}-2,6-difluorobenzene-sulphonamide;
N-{[1-(7-chloro-1,4-benzodioxan-2-ylmethyl)-4-piperidyl]methyl}-4-chlorobenzene-sulphonamide;
N-{[1-(7-trifluoromethyl-1,4-benzodioxan-2-ylmethyl)-4-piperidyl]methyl}pyridine-2-sulphonamide N-{[1-(7-bromo-1,4-benzodioxan-2-ylmethyl)-4-piperidylmethyl}-2,3-dichlorobenzensulphonamide 2,3-dichloro-N-{[1-(7-trifluoromethyl-1,4-benzodioxan-2-ylmethyl)-4piperidyl]methyl}benzenesulphonamide N-{[1-(7-chloro-1,4-benzodioxan-2-ylmethyl)-4-piperidyl]methyl}-2,4-dinitrobenzenesulphonamide N-{[1-(7-chloro-1,4-benzodioxan-2-ylmethyl)-4-piperidyl]methyl}-2,5-bis(2,2,2-trifluoroethoxy)benzenesulphonamide 2-chloro-N-{[1-(7-chloro-1,4-benzodioxan-2-ylmethyl)-4-piperidyl]methyl}-4-trifluoromethylbenzenesulphonamide N-{[1-(7-chloro-1,4-benzodioxan-2-ylmethyl)-4-piperidyl]methyl}-2,4-dinitrobenzene-sulphonamide;

N-{[1-(7-chloro-1,4-benzodioxan-2-ylmethyl)-4-piperidyl]methyl}-2,5-bis(2,2,2-trifluoroethoxy)benzenesulphonamide;

2-chloro-N-{[1-(7-chloro-1,4-benzodioxan-2-ylmethyl)-4-piperidyl]methyl}-4-trifluoromethylbenzenesulphonamide;

N-{[1-(7-chloro-1,4-benzodioxan-2-ylmethyl)-4-piperidyl]methyl}-4-iodobenzenesulphonamide;

N-{[1-(7-chloro-1,4-benzodioxan-2-ylmethyl)-4-piperidyl]methyl}-4-methoxy-2,3,6-trimethylbenzenesulphonamide;

N-{[1-(7-chloro-1,4-benzodioxan-2-ylmethyl)-4-piperidyl]methyl}naphth[2,1-d][1,2, 3]-oxadiazole-5-sulphonamide;

N-{[1-(7-chloro-1,4-benzodioxan-2-ylmethyl)-4-piperidyl]methyl}-2,4,6-trimethylbenzenesulphonamide;

N-{[1-(7-chloro-1,4-benzodioxan-2-ylmethyl)-4-piperidyl]methyl}-2,3,4,5,6-pentamethylbenzenesulphonamide;

N-{[1-(7-chloro-1,4-benzodioxan-2-ylmethyl)-4-piperidyl]methyl}-5-(diethylamino)-naphthalene-1-sulphonamide;

N-{[1-(7-chloro-1,4-benzodioxan-2-ylmethyl)-4-piperidyl]methyl}-4-trifluoromethylbenzenesulphonamide;

N-{[1-(7-chloro-1,4-benzodioxan-2-ylmethyl)-4-piperidyl]methyl}-3-nitrobenzenesulphonamide;

N-{[1-(7-chloro-1,4-benzodioxan-2-ylmethyl)-4-piperidyl]methyl}-4-methyl-3,5-dinitrobenzenesulphonamide;

5-chloro-N-{[1-(7-chloro-1,4-benzodioxan-2-ylmethyl)-4-piperidyl]methyl}-2-methoxybenzenesulphonamide;

N-{[1-(7-chloro-1,4-benzodioxan-2-ylmethyl)-4-piperidyl]methyl}-3-trifluoromethylbenzenesulphonamide;

N-{[1-(7-chloro-1,4-benzodioxan-2-ylmethyl)-4-piperidyl]methyl}-4-trifluoromethoxybenzenesulphonamide;

N-{[1-(7-chloro-1,4-benzodioxan-2-ylmethyl)-4-piperidyl]methyl}-2-naphthalenesulphonamide;

N-{[1-(7-chloro-1,4-benzodioxan-2-ylmethyl)-4-piperidyl]methyl}-1-naphthalenesulphonamide;

N-{[1-(7-chloro-1,4-benzodioxan-2-ylmethyl)-4-piperidyl]methyl}-2,5-dimethoxy-benzenesulphonamide;

N-{[1-(7-chloro-1,4-benzodioxan-2-ylmethyl)-4-piperidyl]methyl}-4-methylbenzenesulphonamide;

N-{[1-(7-chloro-1,4-benzodioxan-2-ylmethyl)-4-piperidyl]methyl}benzenesulphonamide;

N-{[1-(7-chloro-1,4-benzodioxan-2-ylmethyl)-4-piperidyl]methyl}-5-fluoro-2-methyl-benzenesulphonamide;

2,5-dibromo-N-{[1-(7-chloro-1,4-benzodioxan-2-ylmethyl)-4-piperidyl]methyl}-benzenesulphonamide;

N-{[1-(7-chloro-1,4-benzodioxan-2-ylmethyl)-4-piperidyl]methyl}-2-nitrobenzene-sulphonamide;

N-{[1-(7-chloro-1,4-benzodioxan-2-ylmethyl)-4-piperidyl]methyl}-2,3,4-trifluoro-benzenesulphonamide;

2,5-dibromo-N-{[1-(7-chloro-1,4-benzodioxan-2-ylmethyl)-4-piperidyl]methyl}-3,6-difluorobenzenesulphonamide;

N-{[1-(7-chloro-1,4-benzodioxan-2-ylmethyl)-4-piperidyl]methyl}-2-fluorobenzenesulphonamide;

2-chloro-N-{[1-(7-chloro-1,4-benzodioxan-2-ylmethyl)-4-piperidyl]methyl}-benzenesulphonamide;

3-chloro-N-{[1-(7-chloro-1,4-benzodioxan-2-ylmethyl)-4-piperidyl]methyl}-4-fluoro-benzenesulphonamide;

2,3-dichloro-N-{[1-(7-chloro-1,4-benzodioxan-2-ylmethyl)-4-piperidyl]methyl}benzenesulphonamide;

4-acetamido-N-{[1-(7-bromo-1,4-benzodioxan-2-ylmethyl)-4-piperidyl]methyl}-benzenesulphonamide;

N-{[1-(7-bromo-1,4-benzodioxan-2-ylmethyl)-4-piperidyl]methyl}-2-fluorobenzenesulphonamide;

N-{[1-(7-bromo-1,4-benzodioxan-2-ylmethyl)-4-piperidyl]methyl}-2-chlorobenzenesulphonamide;

N-{[1-(7-bromo-1,4-benzodioxan-2-ylmethyl)-4-piperidyl]methyl}-2,4-difluorobenzenesulphonamide;

3-chloro-N-{[1-(7-bromo-1,4-benzodioxan-2-ylmethyl)-4-piperidyl]methyl}-4-fluorobenzenesulphonamide;

2,3-dichloro-N-{[1-(6,7-methylenedioxy-1,4-benzodioxan-2-ylmethyl)-4-piperidyl]methyl}benzenesulphonamide;

and pharmaceutically acceptable salts thereof in the form of individual enantiomers, racemates, or other mixtures Specific enantiomers.

Specific enantiomeric forms of compounds of formula I include:

(S)-N-{[1-(7-chloro-1,4-benzodioxan-2-ylmethyl)-4-piperidyl]methyl}pyridine-2-sulphonamide;

(S)-4-[N-(7-chloro-1,4-benzodioxan-2-ylmethyl)aminomethyl]-1-(2-pyridinesulphonyl)-piperidine);

(S)-N-{[1-(7-chloro-1,4-benzodioxan-2-ylmethyl)-4-piperidyl]methyl}pyridine-3-sulphonamide;

(S)-N-{[1-(7-chloro-1,4-benzodioxan-2-ylmethyl)-4-piperidyl]methyl}-4-nitrobenzene-sulphonamide;

(S)-N-{[1-(7-chloro-1,4-benzodioxan-2-ylmethyl)-4-piperidyl]methyl}-4-fluorobenzene-sulphonamide;

(S)-N-{[1-(7-chloro-1,4-benzodioxan-2-ylmethyl)-4-piperidyl]methyl}-3,4-dimethoxy-benzenesulphonamide;

(S)-N-{[1-(7-chloro-1,4-benzodioxan-2-ylmethyl)-4-piperidyl]methyl}-2,4-difluoro-benzenesulphonamide;

(S)-4-acetamido-N-{[1-(7-chloro-1,4-benzodioxan-2-ylmethyl)-4-piperidyl]methyl}-benzenesulphonamide;

(S)-N-{[1-(7-chloro-1,4-benzodioxan-2-ylmethyl)-4-piperidyl]methyl}-4-methoxy benzenesulphonamide;

(S)-N-{[1-(7-chloro-1,4-benzodioxan-2-ylmethyl)-4-piperidyl]methyl}-2,6-difluoro-benzenesulphonamide;

(S)-N-{[1-(7-chloro-1,4-benzodioxan-2-ylmethyl)-4-piperidyl]methyl}-4-chloro-benzenesulphonamide;

(S)-N-{[1-(7-trifluoromethyl-1,4-benzodioxan-2-ylmethyl)-4-piperidyl]methyl}-pyridine-2-sulphonamide (S)-N-{[1-(7-bromo-1,4-benzodioxan-2-ylmethyl)-4-piperidyl]methyl}-2,3-dichlorobenzensulphonamide (S)-2,3-dichloro-N-{(1-7-(trifluoromethyl-1,4-benzodioxan-2-ylmethyl)-4-piperidyl]-methyl}benzenesulphonamide (S)-N-{[1-(7-chloro-1,4-benzodioxan-2-ylmethyl)-4-piperidyl]methyl}-2,4-dinitro-benzenesulphonamide;

(S)-N-{[1-(7-chloro-1,4-benzodioxan-2-ylmethyl)-4-piperidyl]methyl}-2,5-bis(2,2,2-trifluoroethoxy)benzenesulphonamide;

(S)-2-chloro-N-{[1-(7-chloro-1,4-benzodioxan-2-ylmethyl)-4-piperidyl]methyl}-4-trifluoromethylbenzenesulphonamide;

(S)-N-{[1-(7-chloro-1,4-benzodioxan-2-ylmethyl)-4-piperidyl]methyl}-4-iodobenzene-sulphonamide;

(S)-N-{[1-(7-chloro-1,4-benzodioxan-2-ylmethyl)-4-piperidyl]methyl}-4-methoxy-2,3,6-trimethylbenzenesulphonamide;

(S)-N-{[1-(7-chloro-1,4-benzodioxan-2-ylmethyl)-4-piperidyl]methyl}naphth[2,1-d][1,2,3]oxadiazole-5-sulphonamide;
(S)-N-{[1-(7-chloro-1,4-benzodioxan-2-ylmethyl)-4-piperidyl]methyl}-2,4,6-trimethyl-benzenesulphonamide;
(S)-N-{[1-(7-chloro-1,4-benzodioxan-2-ylmethyl)-4-piperidyl]methyl}-2,3,4,5,6-pentamethylbenzenesulphonamide;
(S)-N-{[1-(7-chloro-1,4-benzodioxan-2-ylmethyl)-4-piperidyl]methyl}-5-(diethyl-amino)naphthalene-1-sulphonamide;
(S)-N-{[1-(7-chloro-1,4-benzodioxan-2-ylmethyl)-4-piperidyl]methyl}-4-trifluoro-methylbenzenesulphonamide;
(S)-N-{[1-(7-chloro-1,4-benzodioxan-2-ylmethyl)-4-piperidyl]methyl}-3-nitrobenzene-sulphonamide;
(S)-N-{[1-(7-chloro-1,4-benzodioxan-2-ylmethyl)-4-piperidyl]methyl}-4-methyl-3,5-dinitrobenzenesulphonamide;
(S)-5-chloro-N-{[1-(7-chloro-1,4-benzodioxan-2-ylmethyl)-4-piperidyl]methyl}-2-methoxybenzenesulphonamide;
(S)-N-{[1-(7-chloro-1,4-benzodioxan-2-ylmethyl)-4-piperidyl]methyl}-3-trifluoro-methylbenzenesulphonamide;
(S)-N-{[1-(7-chloro-1,4-benzodioxan-2-ylmethyl)-4-piperidyl]methyl}-4-trifluoro-methoxybenzenesulphonamide;
(S)-N-{[1-(7-chloro-1,4-benzodioxan-2-ylmethyl)-4-piperidyl]methyl}-2-naphthalene-sulphonamide;
(S)-N-{[1-(7-chloro-1,4-benzodioxan-2-ylmethyl)-4-piperidyl]methyl}-1-naphthalene-sulphonamide;
(S)-N-{[1-(7-chloro-1,4-benzodioxan-2-ylmethyl)-4-piperidyl]methyl}-2,5-dimethoxy-benzenesulphonamide;
(S)-N-{[1-(7-chloro-1,4-benzodioxan-2-ylmethyl)-4-piperidyl]methyl}-4-methyl-benzenesulphonamide;
(S)-N-{[1-(7-chloro-1,4-benzodioxan-2-ylmethyl)-4-piperidyl]methyl}benzene-sulphonamide;
(S)-N-{[1-(7-chloro-1,4-benzodioxan-2-ylmethyl)-4-piperidyl]methyl}-5-fluoro-2-methylbenzenesulphonamide;
(S)-2,5-dibromo-N-{[1-(7-chloro-1,4-benzodioxan-2-ylmethyl)-4-piperidyl]methyl}-benzenesulphonamide;
(S)-N-{[1-(7-chloro-1,4-benzodioxan-2-ylmethyl)-4-piperidyl]methyl}-2-nitro-benzenesulphonamide;
(S)-N-{[1-(7-chloro-1,4-benzodioxan-2-ylmethyl)-4-piperidyl]methyl}-2,3,4-trifluoro-benzenesulphonamide;
(S)-2,5-dibromo-N-{[1-(7-chloro-1,4-benzodioxan-2-ylmethyl)-4-piperidyl]methyl}-3,6-difluorobenzenesulphonamide;
(S)-N-{[1-(7-chloro-1,4-benzodioxan-2-ylmethyl)-4-piperidyl]methyl}-2-fluorobenzenesulphonamide;
(S)-2-chloro-N-{[1-(7-chloro-1,4-benzodioxan-2-ylmethyl)-4-piperidyl]methyl}benzenesulphonamide;
(S)-3-chloro-N-{[1-(7-chloro-1,4-benzodioxan-2-ylmethyl)-4-piperidyl]methyl}-4-fluoro-benzenesulphonamide;
(S)-2,3-dichloro-N-{[1-(7-chloro-1,4-benzodioxan-2-ylmethyl)-4-piperidyl]methyl}-benzenesulphonamide;
(S)-4-acetamido-N-{[1-(7-bromo-1,4-benzodioxan-2-ylmethyl)-4-piperidyl]methyl}-benzenesulphonamide;
(S)-N-{[1-(7-bromo-1,4-benzodioxan-2-ylmethyl)-4-piperidyl]methyl}-2-fluorobenzenesulphonamide;
(S)-N-{[1-(7-bromo-1,4-benzodioxan-2-ylmethyl)-4-piperidyl]methyl}-2-chlorobenzenesulphonamide;
(S)-N-{[1-(7-bromo-1,4-benzodioxan-2-ylmethyl)-4-piperidyl]methyl}-2,4-difluorobenzenesulphonamide;
(S)-3-chloro-N-{[1-(7-bromo-1,4-benzodioxan-2-ylmethyl)-4-piperidyl]methyl}-4-fluorobenzenesulphonamide;
(S)-2,3-dichloro-N-{[1-(6,7-methylenedioxy-1,4-benzodioxan-2-ylmethyl)-4-piperidyl]methyl}benzenesulphonamide;
and pharmaceutically acceptable salts thereof.

A particularly preferred compound is N-{[1-(7-bromo-1,4-benzodioxan-2-ylmethyl)-4-piperidyl]methyl}-2,3-dichlorobenzensulphonamide including enantiomers and pharmaceutically acceptable salts thereof.

It will be appreciated by those skilled in the art that the term "1,4-benzodioxan" as used in the above lists and throughout this specification is synonymous with the term "2,3-dihydro-1,4-benzodioxin".

The present invention also includes pharmaceutical compositions containing a therapeutically effective amount of a compound of formula I or a salt thereof together with a pharmaceutically acceptable diluent or carrier.

As used hereinafter, the term "active compound" denotes a compound of formula I or a salt thereof. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1–500 mg. The excipients used in the preparation of these compositions are the excipients known in the pharmacist's art.

Compositions for oral administration are the preferred compositions of the invention and these are the known pharmaceutical forms for such administration, for example tablets, capsules, syrups and aqueous or oil suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions of the invention suitable for rectal administration are the known pharmaceutical forms for such administration, for example, suppositories with cocoa butter or polyethylene glycol bases.

Pharmaceutical compositions may also be administered parenterally (for example subcutaneously, intramuscularly, intradermally and/or intravenously [such as by injection and/or infusion]) in the known pharmaceutical dosage forms for parenteral administration (for example sterile suspensions in aqueous and/or oily media and/or sterile solutions in suitable solvents, preferably isotonic with the blood of the intended patient). Parenteral dosage forms may be sterilised (for example by micro-filtration and/or using suitable sterilising agents [such as ethylene oxide]). Optionally one or more of the following pharmaceutically acceptable adjuvants suitable for parenteral administration may be added to parenteral dosage forms: local anaesthetics, preservatives, buffering agents and/or mixtures thereof. Parenteral dosage forms may be stored in suitable sterile sealed containers (for example ampoules and/or vials) until use. To enhance stability during storage the parenteral dosage form may be frozen after filling the container and fluid (for example water) may be removed under reduced pressure.

Pharmaceutical compositions may be administered nasally in known pharmaceutical forms for such administration (for example sprays, aerosols, nebulised solutions and/or powders). Metered dose systems known to those skilled in the art (for example aerosols and/or inhalers) may be used.

Pharmaceutical compositions may be administered to the buccal cavity (for example sub-lingually) in known pharmaceutical forms for such administration (for example slow dissolving tablets, chewing gums, troches, lozenges, pastilles, gels, pastes, mouthwashes, rinses and/or powders).

Compositions for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, for example paraffin wax or beeswax, together with a potential transdermal accelerant such as dimethyl sulphoxide or propylene glycol. Alternatively the active compounds may be dispersed in a pharmaceutically acceptable cream or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or ester or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The present invention also comprises the use of a compound of formula I as a medicament.

The compounds of formula I or salts thereof or pharmaceutical compositions containing a therapeutically effective amount of a compound of formula I or a salt thereof may be used to treat depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders, anorexia, cardiovascular and cerebrovascular disorders, non-insulin dependent diabetes mellitus, hyperglycaemia, constipation, arrhythmia, disorders of the neuroendocrine system, stress, and spasticity in human beings. Whilst the precise amount of active compound administered in such treatment will depend on a number of factors, for example the age of the patient, the severity of the condition and the past medical history and always lies within the sound discretion of the administering physician, the amount of active compound administered per day is in the range 1 to 1000 mg preferably 5 to 500 mg given in single or divided doses at one or more times during the day.

A further aspect of the present invention provides the use of a compound of formula I in the manufacture of a medicament for treating depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, or spasticity in human beings.

The present invention also provides a method of treating depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, or spasticity in human beings which comprises the administration of a therapeutically effective amount of a compound of formula I to a patient in need thereof.

Processes for the preparation of compounds of formula I will now be described. These processes form a further aspect of the present invention. The processes are preferably carried out at atmospheric pressure, at a temperature in the range 0–200° C., preferably in the range 20–150° C. The substituents are as defined for formula I above unless otherwise stated.

Compounds of formula I in which Q is a group of formula IIa in which $R_5$ is H and V is $(CH_2)_n$ wherein n is 1,2 or 3, may be prepared by reaction of a compound of formula III

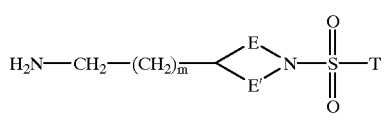
III in which m is 0, 1 or 2, with a compound of formula IV

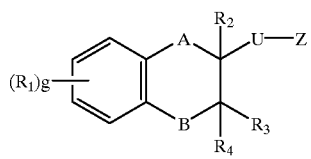
IV in which Z is a leaving group, for example toluene-4-sulphonyloxy, optionally in the presence of a suitable solvent, for example acetonitrile, optionally in the presence of a base, for example potassium carbonate, and optionally in the presence of a catalyst, for example potassium iodide.

Compounds of formula III may be prepared by reaction of a compound of formula V

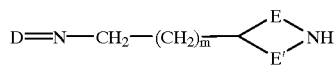
V in which D is a protecting group, for example benzylidene, with a sulphonylating agent of formula $X-SO_2-T$ in which X is a leaving group, for example halo or hydroxy in the presence of a base, for example triethylamine, in a suitable solvent, for example dichloromethane, followed by removal of the protecting group, for example by acid-catalysed hydrolysis.

Compounds of formula IV in which Z is toluene-4-sulphonyloxy, may be prepared by reaction of a compound of formula VI

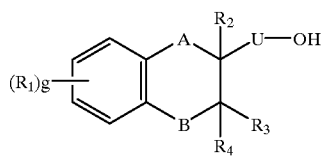
VI with toluene-4-sulphonyl chloride, optionally in the presence of a base, for example pyridine.

Compounds of formula VI in which A and B are both —O—, U is methylene, and $R_2$, $R_3$ and $R_4$ are all H, may be prepared by cyclisation of a compound of formula VII

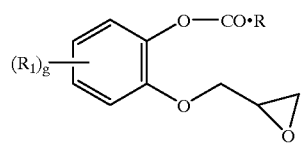
VII in which R is H or an alkyl group containing 1 to 4 carbon atoms, using a base, for example potassium carbonate.

Compounds of formula VII may be prepared by oxidation of a compound of formula VIII

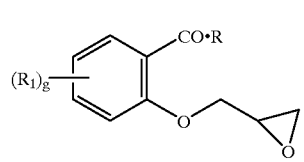
VIII in which R is H or an alkyl group containing 1 to 4 carbon atoms, with a peroxyacid, for example 3-chloroperoxybenzoic acid.

Compounds of formula VII may be prepared by alkylating a compound of formula IX

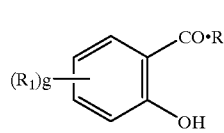
IX in which R is H or an alkyl group containing 1 to 4 carbon atoms, with a compound of formula X

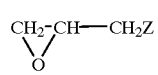
X in which Z is a leaving group, for example chloro or toluene-4-sulphonyloxy, in a suitable solvent, for example dimethylformamide, in the presence of a base, for example potassium carbonate. When the appropriate enantiomerically pure form of a compound of formula X, for example (R)-glycidyl 4-toluenesulphonate, is used, the single (S)-enantiomer of a compound of formula VI can be prepared.

Compounds of formula I in which U is methylene and Q is a group of formula IIa in which $R_5$ is H and V is $(CH_2)_n$ wherein n is 1, 2 or 3, may be prepared by reaction of a compound of formula XI

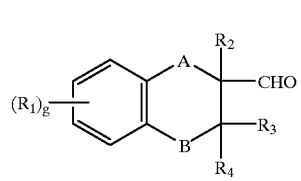
XI with a compound of formula III, followed by reduction of the intermediate imine with a suitable reducing agent, for example, sodium borohydride.

Compounds of formula XI may be prepared by oxidation of a compound of formula VI in which U is methylene, with a suitable oxidising agent, for example pyridinium chlorochromate.

Compounds of formula I in which Q is a group of formula IIb may be prepared by reaction of a compound of formula XII

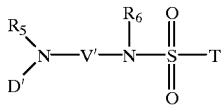

XII in which D' is H, with a compound of formula IV in which Z is a leaving group, for example toluene-4-sulphonyloxy, optionally in the presence of a base, for example potassium carbonate, optionally in the presence of a suitable solvent, for example acetonitrile, and optionally in the presence of a catalyst, for example potassium iodide.

Compounds of formula XII in which D' is H may be prepared by deprotection of a compound of formula XII in which D' is a protecting group, for example tert-butoxycarbonyl, for example by hydrolysis in the presence of an acid, for example trifluoroacetic acid.

Compounds of formula XII in which D' is a protecting group may be prepared by reaction of a compound of formula XIII

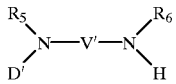

XIII in which D' is a protecting group, for example tert-butoxycarbonyl, with a compound of formula X—SO$_2$—T in which X is a leaving group, for example halo or hydroxy, in the presence of a base, for example triethylamine in a suitable solvent such as dichloromethane.

Compounds of formula I in which Q is a group of formula IIc in which V is (CH$_2$)$_n$ wherein n is 1, 2 or 3, may be prepared by reaction of a compound of formula XIV

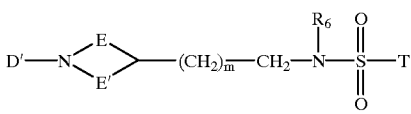

XIV in which D' is H and m is 0, 1 or 2, with a compound of formula IV in which Z is a leaving group, for example toluene-4-sulphonyloxy, optionally in the presence of a base, for example potassium carbonate, optionally in the presence of a suitable solvent, for example acetonitrile, and optionally in the presence of a catalyst, for example potassium iodide.

Compounds of formula XIV in which D' is H may be prepared by deprotection of a compound of formula XIV in which D' is a protecting group, for example tert-butoxycarbonyl, for example by hydrolysis in the presence of an acid, for example trifluoroacetic acid.

Compounds of formula XIV in which D' is a protecting group may be prepared by reaction of a compound of formula XV

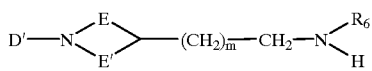

XV in which D' is a protecting group, for example tert-butoxycarbonyl, and m is 0, 1 or 2, with a compound of formula X—SO$_2$—T in which X is a leaving group, for example halo or hydroxy, in the presence of a base, for example triethylamine in a suitable solvent such as dichloromethane.

Compounds of formula I in which Q is a group of formula IIc may also be prepared by reaction of a compound of formula XVI

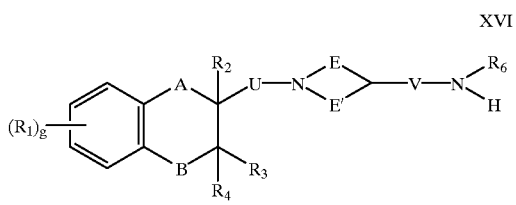

XVI with a sulphonylating agent of formula X—SO$_2$—T in which X is a leaving group, for example halo or hydroxy, in the presence of a base, for example triethylamine, in a suitable solvent, for example dichloromethane.

Compounds of formula XVI in which R$_6$ is H may be prepared from compounds of formula XVII

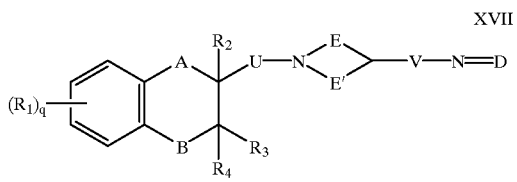

XVII in which D is a protecting group, for example 5-bromo-2-hydroxybenzylidene, by acid or base catalysed hydrolysis.

Compounds of formula XVII may be prepared by reaction of a compound of formula XVIII

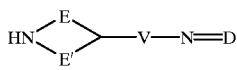

XVIII in which D is a protecting group, for example 5-bromo-2-hydroxybenzylidene with a compound of formula IV, optionally in the presence of a base, for example triethylamine.

Compounds of formula XVIII may be prepared by reaction of a compound of formula XIX

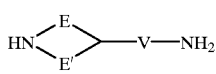

XIX with a protecting reagent, for example 5-bromo-2-hydroxybenzaldehyde.

Compounds of formula I in which R$_5$ is an alkyl group may also be prepared by alkylation of a compound of formula I in which R$_5$ is H with, for example, formaldehyde and formic acid, or an aldehyde and a reducing agent such as sodium cyanoborohydride.

The ability of compounds of formula I to interact with 5-hydroxytryptamine (5-HT) receptors has been demonstrated by the following test which determines the ability of the compounds to inhibit tritiated ligand binding to 5-HT receptors in vitro and in particular to 5-HT$_{1A}$ receptors.

Hippocampal tissue from the brains of male Charles River CD rats weighing between 150–250 g were homogenised in ice-cold 50 mM Tris-HCl buffer (pH 7.7) when measured at 25° C., 1:40 w/v) and centrifuged at 30,000 g at 4° C. for 10 minutes. The pellet was rehomogenised in the same buffer, incubated at 37° C. for 10 minutes and centrifuged at 30,000 g at 4° C. for 10 minutes. The final pellet was resuspended in 50 mM Tris-HCl buffer (pH 7.7) containing 4 mM CaCl$_2$, 0.1% L-ascorbic acid and 10 μM pargyline hydrochloride (equivalent to 6.25 mg wet weight of tissue/ml) and used immediately in the binding assay. Aliquots (400 μl; equivalent to 2.5 mg wet weight of tissue/tube) of this suspension were added to tubes containing the ligand (50 μl; 2 nM) and distilled water (50 μl; total binding) or 5-HT (50 μl; 10 μM; non-specific binding) or test compound (50 μl; at a single concentration of $10^{-6}$ M or at 10 concentrations ranging from $10^{-11}$–$10^{-3}$ M). The ligand was [$^3$H]8-hydroxy-2-(dipropylamino)tetralin ([$^3$H]8-OH-DPAT) and the mixture was incubated at 25° C. for 30 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$ M) of test compound. Displacement curves were then produced for those compounds which displaced ≧50% of specific binding of the tritiated ligand at $10^{-6}$ M using a range of concentrations of the compound. The concentration which gave 50% inhibition of specific binding (IC$_{50}$) was obtained from the curve. The inhibition coefficient Ki was then calculated using the formula $$K_i = \frac{IC50}{1 + ([ligand]/K_D)}$$

in which [ligand] is the concentration of the tritiated ligand used and $K_D$ Is the equilibrium dissociation constant for the ligand.

The ability of compounds of formula I to interact with dopamine receptors has been demonstrated by the following test which determines the ability of the compounds to inhibit tritiated ligand binding to dopamine receptors in vitro and in particular to the D$_2$-like dopamine receptors.

Striatal tissue from the brains of male Charles River CD rats weighing between 140–250 g were homogenised in ice-cold 50 mM Tris-HCl buffer (pH 7.7 when measured at 25° C.) and centrifuged at 40,000 g for 10 minutes. The pellet was resuspended in Tris salts buffer ( 50 mM Tris-HCl buffer containing 120 mM NaCl, 5 mM KCl, 2 mM CaCl$_2$ and 1 mM MgCl$_2$ with the addition of 6 mM ascorbic acid; pH 7.7 when measured at 25° C.), and again centrifuged at 40,000 g for 10 minutes. The final pellet was stored at −80° C. Before each test the pellet was resuspended in Tris salts buffer (equivalent to 2 mg wet weight of tissue/ml). Aliquots (720 μl; equivalent to 1.44 mg wet weight of tissue/tube) of this suspension were then added to tubes containing the ligand (40 μl; 1 nM) and Tris salts buffer (40 μl; total binding) or spiroperidol (40 μl; 10 nM; non-specific binding) or test compound (40 μl; at a single concentration of $10^{-6}$ M or at 6 concentrations ranging from $10^{-11}$–$10^{-4}$M). The ligand was tritiated (S)-sulpiride and the mixture was incubated at 4° C. for 40 minutes before the incubation was terminated by rapid filtration.

The filters were washed with ice-cold Tris-HCl buffer and dried. The filters were punched out in to vials, scintillation fluid added and were left for about 20 hours before being counted by scintillation spectrophotometry. The percentage displacement of specific binding of the tritiated ligand was calculated for the single concentration ($10^{-6}$M) of test compound. Displacement curves were then produced over a range of concentrations for those compounds which displaced ≧50% of specific binding of the tritiated ligand at $10^{-6}$M. The concentration which gave a 50% inhibition of specific binding (IC50) was obtained from the curve. The inhibition coefficient Ki was then calculated using the formula $$K_i = \frac{IC50}{1 + ([ligand]/K_D)}$$

in which [ligand] is the concentration of the tritiated ligand used and $K_D$ is the equilibrium dissociation constant for the ligand.

The $K_i$ values obtained in the above tests for 5-HT$_{1A}$, and D$_2$-like binding for each of the final products of the Examples hereinafter are given in Table I below.

TABLE 1

| | Ki (nM) value for | |
|---|---|---|
| Example Number | 5-HT$_{1A}$ | D$_2$-like |
| 1 | 86.8 | 29.4 |
| 2 | 11.4 | 27.9 |
| 3 | 31.6 | 28 |
| 4 | 15 | 105 |
| 5 | 37 | 69.8 |
| 6 | 20 | 40.2 |
| 7 | 35 | 37.8 |
| 8 | 45 | 37.2 |
| 9 | 42 | 96.4 |
| 10 | 7.4 | 50.1 |
| 11 | 69 | 157 |
| 12 | 30 | 28.7 |
| 13 | 20 | 102 |
| 14 | 25 | 111 |
| 15 | 82% | 212 |
| 16 | 84% | 258 |
| 17 | 88% | 519 |
| 18 | 90% | 227 |
| 19 | 55% | 306 |
| 20 | 75% | 235 |
| 21 | 71% | 249 |
| 22 | 59% | 317 |
| 23 | 82% | 83% |
| 24 | 90% | 533 |
| 25 | 91% | 119 |
| 26 | 88% | 87% |
| 27 | 68% | 351 |
| 28 | 68% | 352 |
| 29 | 67% | 357 |
| 30 | 65% | 241 |
| 31 | 60% | 215 |
| 32 | 87% | 285 |
| 33 | 91% | 301 |
| 34 | 87% | 88 |
| 35 | 81% | 328 |
| 36 | 68% | 487 |
| 37 | 87% | 85 |
| 38 | 95% | 330 |
| 39 | 98% | 438 |
| 40 | 93% | 107% |

TABLE 1-continued

| Example Number | Ki (nM) value for | |
|---|---|---|
| | 5-HT$_{1A}$ | D$_2$-like |
| 41 | 93% | 106% |
| 42 | 80% | 84% |
| 43 | 1.5 | 73 |
| 44 | 14 | 23 |
| 45 | 97% | 109% |
| 46 | 96% | 106% |
| 47 | 16 | 48 |
| 48 | 88% | 103% |
| 49 | 77% | 89% |

The % figures in Table 1 are for % displacement at 10$^{-6}$ M.

Advantageous compounds of the present invention have a Ki of less than 100 nM for 5-HT$_{1A}$ or a binding affinity for 5-HT$_{1A}$ of greater than 90% at 10$^{-6}$M and a Ki of less than 100 nM for D$_2$-like receptors or a binding affinity for D$_2$-like receptors of greater than 90% at 10$^{-6}$M.

The invention is illustrated by the following Examples which are given by way of example only. The final products of the Examples were characterised by one or more of the following procedures: gas-liquid chromatography; high performance liquid chromatography; elemental analysis, nuclear magnetic resonance spectroscopy and infrared spectroscopy.

EXAMPLE 1

Pyridine (1.85 ml) was added to a stirred solution of 4-(aminomethyl)-1-(tert-butoxycarbonyl)piperidine (4.46 g) and pyridine-2-sulphonyl chloride (3.7 g) in dichloromethane (110 ml) at −10° C. under a nitrogen atmosphere. The reaction was then warmed to ambient temperature over 16 hours and poured into water (300 ml). The organic layer was separated and further washed with hydrochloric acid (1 M, 2×200 ml), saturated aqueous sodium bicarbonate solution (200 ml) and brine (200 ml). After drying over anhydrous magnesium sulphate, the solution was evaporated to dryness to afford N-{[1-(tert-butoxycarbonyl)-4-piperidyl]methyl}pyridine-2-sulphonamide (3.5 g) as an oil.

Trifluoroacetic acid (12.5 ml) was added to a solution of the product from the previous reaction (2.0 g) in dichloromethane (12.5 ml) and the mixture stirred at ambient temperature for 4 hours. The solvent was removed under reduced pressure to yield crude N-4-piperidylmethyl)pyridine-2-sulphonamide trifluoroacetate.

A stirred mixture of this material, (R)-7-chloro-1,4-benzodioxan-2-ylmethyl 4-toluenesulphonate (1.77 g, prepared as described in WO97/03071), potassium carbonate (7.6 g), and potassium iodide (10 mg) in acetonitrile (150 ml) was heated at reflux, under nitrogen, for 60 hours. The reaction was cooled, filtered and concentrated under reduced pressure to afford a brown viscous oil (5.8 g) which was purified by flash chromatography on silica gel eluting with neat ethyl acetate. The appropriate fractions were combined and the solvent removed under reduced pressure to give a colourless oil (0.6 g). Hydrogen chloride gas was bubbled through a solution of the oil in a mixture of dichloromethane (10 ml) and diethyl ether (20 ml), until pH 1 was achieved. The solvent was removed under reduced pressure and the resulting hygroscopic yellow gum was immediately dried at 80° C. under reduced pressure to afford (S)-(−)-N-{[1-(7-chloro-1,4-benzodioxan-2-ylmethyl)-4-piperidyl]methyl}pyridine-2-sulphonamide monohydrochloride 0.6 hydrate as a cream solid foam (0.5 g); m.p. 143° C. (dec.), $[\alpha]_D^{23}$−51.6° (c=1.03, MeOH).

EXAMPLE 2

Triethylamine (6.3 ml) was added to a cloudy solution of N-benzylidene-4-piperidylmethylamine (4.05 g) and pyridine-2-sulphonyl chloride (4.0 g) in dichloromethane (100 ml) and the resulting clear yellow solution was stirred for 14 hours. Removal of the solvent under reduced pressure gave a yellow solid which on addition of diethyl ether (100 ml) partly dissolved. The insoluble white solid (triethylamine hydrochloride) was removed by filtration. Evaporation of the filtrate afforded a flocculent yellow solid which recrystallised from ethanol to give 4-[N-(benzylidene)aminomethyl]-1-(2-pyridinesulphonyl)piperidine as a white crystalline solid (4.7 g).

A solution of the product from the previous reaction (4.5 g) and potassium hydrogen sulphonate (8.76 g) in water (110 ml) was stirred for 20 hours. The reaction was washed with diethyl ether (3×100 ml), basified to pH 14 using aqueous sodium hydroxide solution (5 M) and extracted with diethyl ether (4×100 ml). These latter ethereal layers were combined, dried over anhydrous magnesium sulphate and evaporated to dryness to give crude 4-(aminomethyl)-1-(2-pyridinesulphonyl)piperidine as a yellow oil (2.7 g).

A stirred mixture of this material, (R)-7-chloro-1,4-benzodioxan-2-ylmethyl 4-toluenesulphonate, potassium carbonate (2.73 g) and potassium iodide (10 mg) in acetonitrile (125 ml) was heated at reflux, under nitrogen, for 20 hours. The reaction was cooled and stirred at ambient temperature for a further 24 hours. Excess potassium carbonate was removed by filtration and the filtrate concentrated under reduced pressure. Purification by flash chromatography on silica gel eluting with a 19:1 mixture of ethyl acetate and methanol afforded a yellow oil (2.1 g). Trituration with diethyl ether (50 ml) gave (S)-(−)-4-[N-(7-chloro-1,4-benzodioxan-2-ylmethyl)aminomethyl]-1-(2-pyridinesulphonyl)piperidine 0.8 hydrate as an off-white solid (1.68 g); m.p. 71–74° C., $[\alpha]_D^{22}$−40.9° (c=0.33, MeOH).

EXAMPLE 3

Triethylamine (2.4 ml) was added to an orange solution of (S)-4-(aminomethyl)-1-(7-chloro-1,4-benzodioxan-2-ylmethyl)piperidine (1.67 g, prepared as described in WO97/03071) and pyridine-3-sulphonyl chloride (2.0 g) in dichloromethane (60 ml) under nitrogen and the solution stirred for 3 hours. The reaction was concentrated under reduced pressure then purified by flash chromatography on silica gel eluting with a 9:1 mixture of dichloromethane and methanol to give an orange oil (2.0 g). Trituration with hot diethyl ether afforded (S)-(−)-N-{[1-(7-chloro-1,4-benzodioxan-2-ylmethyl)-4-piperidyl]methyl}pyridine-3-sulphonamide 0.8 hydrate as a pale pink solid (1.2 g); m.p. 127–128° C., $[\alpha]_D^{22}$−38.5° (c=1.02, MeOH).

EXAMPLE 4

Triethylamine (0.62 ml) was added to a cloudy solution of (S)-4-(aminomethyl)-1-(7-chloro-1,4-benzodioxan-2-ylmethyl)piperidine (0.44 9) and 4-nitrobenzenesulphonyl chloride (0.65 g) in dichloromethane (22 ml) under nitrogen. The resulting solution was stirred for 3 hours then left to stand for 14 hours. The reaction was diluted with dichloromethane (100 ml), washed with water (100 ml) and brine (100 ml), dried over anhydrous magnesium sulphate and concentrated under reduced pressure to afford an orange oil (0.95 g). Purification by flash chromatography on silica gel eluting with a 19:1 mixture of dichloromethane and methanol gave (S)-(−)-N-{[1-(7-chloro-1,4-benzodioxan-2-ylmethyl)-4-piperidyl]-methyl}-4-nitrobenzenesulphonamide as a light brown solid (0.5 g); m.p. 147–148° C., $[\alpha]_D^{22.5}$ −23.5° (c=1.01, CH$_2$Cl$_2$).

EXAMPLE 5

Triethylamine (0.62 ml) was added to a solution of (S)-4-(aminomethyl)-1-(7-chloro-1,4-benzodioxan-2-ylmethyl)piperidine (0.44 g) and 4-fluorobenzenesulphonyl chloride (0.65 g) in dichloromethane (22 ml) under nitrogen and stirred for 3 hours. The reaction was left to stand for 14 hours then diluted with dichloromethane (100 ml), washed with water (100 ml) and brine (100 ml), dried over anhydrous magnesium sulphate and concentrated under reduced pressure. Purification by flash chromatography on silica gel eluting with a 19:1 mixture of dichloromethane and methanol gave a yellow oil which on trituration with diethyl ether yielded (S)-(−)-N-{[1-(7-chloro-1,4-benzodioxan-2-ylmethyl)-4-piperidyl]methyl}-4-fluorobenzenesulphonamide as a yellow solid (0.4 g); m.p. 127–129° C., $[\alpha]_D^{22}$ −41.3° (c=0.72, MeOH).

EXAMPLE 6

Triethylamine (0.62 ml) was added to a solution of (S)-4-(aminomethyl)-1-(7-chloro-1,4-benzodioxan-2-ylmethyl)piperidine (0.44 g) and 3,4-dimethoxybenzenesulphonyl chloride (0.65 g) in dichloromethane (22 ml) under nitrogen. The reaction was stirred for 3 hours then left to stand for 14 hours prior to the addition of dichloromethane (100 ml). The solution was then washed with water (2×30 ml) and brine (2×50 ml), dried over anhydrous magnesium sulphate and concentrated under reduced pressure to afford a brown oil. Purification by flash chromatography on silica gel eluting with a 40:1 mixture of dichloromethane and methanol gave a colourless oil (0.48 g) which crystallised on standing. Trituration with diethyl ether yielded (S)-(−)-N-{[1-(7-chloro-1,4-benzodioxan-2-ylmethyl)-4-piperidyl]methyl}-3,4-dimethoxybenzenesulphonamide as a white solid (0.3 g); m.p. 99–101° C., $[\alpha]_D^{23}$ −41.0° (c=0.52, MeOH).

EXAMPLE 7

Triethylamine (0.62 ml) was added to a solution of (S)-4-(aminomethyl)-1-(7-chloro-1,4-benzodioxan-2-ylmethyl)piperidine (0.44 g) and 2,4-difluorobenzenesulphonyl chloride (0.62 g) in dichloromethane (22 ml) under nitrogen. The reaction was stirred for 3 hours then left to stand for 14 hours. Dichloromethane (100 ml) was added and the reaction was washed with water (2×30 ml) and brine (2×50 ml). The mixture was dried over anhydrous magnesium sulphate and concentrated under reduced pressure to afford a brown oil. Purification by flash chromatography on silica gel eluting with a 40:1 mixture of dichloromethane and methanol gave a yellow oil (0.30 g). Trituration with diethyl ether yielded (S)-(−)-N-{[1-(7-chloro-1,4-benzodioxan-2-ylmethyl)-4-piperidyl]methyl}-2,4-difluorobenzenesulphonamide as a beige solid (0.14 g); m.p. 119–121 ° C., $[\alpha]_D^{23}$ −41.4° (c=0.16, MeOH).

EXAMPLE 8

Triethylamine (0.62 ml) was added to a cloudy solution of (S)-4-(aminomethyl)-1-(7-chloro-1,4-benzodioxan-2-ylmethyl)piperidine (0.44 g) and 4-acetamidobenzenesulphonyl chloride (0.65 g) in dichloromethane (22 ml) under nitrogen. The resulting solution was stirred for 20 hours, diluted with dichloromethane (100 ml) and washed with water (100 ml) and brine (100 ml). After drying over anhydrous magnesium sulphate, the mixture was concentrated under reduced pressure to afford an orange oil. Purification by flash chromatography on silica gel eluting with a 15:1 mixture of dichloromethane and methanol gave an orange gum. Trituration with diethyl ether (20 ml) yielded (S)-(−)-4-acetamido-N-{[1-(7-chloro-1,4-benzodioxan-2-ylmethyl)-4-piperidyl]methyl}benzenesulphonamide as a pale orange solid (0.34 g); m.p. 173–176° C., $[\alpha]_D^{22}$ −39.3° (c=0.37, MeOH).

EXAMPLE 9

Triethylamine (0.62 ml) was added to a solution of (S)-4-(aminomethyl)-1-(7-chloro-1,4-benzodioxan-2-ylmethyl)piperidine (0.44 g) and 4-methoxybenzenesulphonyl chloride (0.61 g) in dichloromethane (22 ml) under nitrogen. The reaction was stirred for 20 hours, diluted with dichloromethane (100 ml) and washed with water (100 ml) and brine (100 ml). After drying over anhydrous magnesium sulphate, the mixture was concentrated under reduced pressure to afford an orange oil. Purification by flash chromatography on silica gel eluting with a 20:1 mixture of dichloromethane and methanol gave a colourless gum. Trituration with diethyl ether (20 ml) yielded (S)-(−)-N-{[1-(7-chloro-1,4-benzodioxan-2-ylmethyl)-4-piperidyl]-methyl}-4-methoxybenzenesulphonamide as a white solid (0.20 g); m.p. 130–131° C., $[\alpha]_D^{22.5}$ 28.9° (c=0.51, CH$_2$Cl$_2$).

EXAMPLE 10

Triethylamine (0.62 ml) was added to a solution of (S)-4-(aminomethyl)-1-(7-chloro-1,4-benzodioxan-2-ylmethyl)piperidine (0.44 g) and 2,6-difluorobenzenesulphonyl chloride (0.62 g) in dichloromethane (22 ml), under nitrogen, and stirred for 20 hours. The reaction was diluted with dichloromethane (100 ml), washed with water (100 ml) and brine (100 ml), dried over anhydrous magnesium sulphate and concentrated under reduced pressure to afford an orange oil. Purification by flash chromatography on silica gel eluting with a 20:1 mixture of dichloromethane and methanol gave an orange gum. Trituration with petroleum ether (b.p. 40–60° C.) yielded (S)-(−)-N-{[1-(7-chloro-1,4-benzodioxan-2-ylmethyl)-4-piperidyl]methyl}-2,6-difluorobenzenesulphonamide as an off-white solid (0.29 g); m.p. 122–124° C., $[\alpha]_D^{22.5}$ −22.1° (c=1.0, CH$_2$Cl$_2$).

EXAMPLE 11

Triethylamine (0.62 ml) was added to a solution of (S)-4-(aminomethyl)-1-(7-chloro-1,4-benzodioxan-2-ylmethyl)piperidine (0.44 g) and 4-chlorobenzenesulphonyl chloride (0.62 g) in dichloromethane (22 ml), under nitrogen, and stirred for 20 hours. The reaction was diluted with dichloromethane (100 ml), washed with water (100 ml) and brine (100 ml), dried over anhydrous magnesium sulphate and concentrated under reduced pressure. Purification by flash chromatography on silica gel eluting with a 20:1 mixture of dichloromethane and methanol gave (S)-(−)-N-{[1-(7-chloro-1,4-benzodioxan-2-ylmethyl)-4-piperidyl]methyl}-4-chlorobenzene-sulphonamide as a white solid (0.30 g); m.p. 152–154° C., $[\alpha]_D^{22.5}$ −23.8° (c=0.97, CH$_2$Cl$_2$).

EXAMPLE 12

Trifluoroacetic acid (10 ml) was added to a solution of N-{[1-(tert-butoxycarbonyl)-4-piperidyl]methyl}pyridine- 2-sulphonamide (1.45 g) in dichloromethane (10 ml) and the mixture stirred at ambient temperature for 1.5 hours. The solvent was removed under reduced pressure to yield crude N-(4-piperidyl methyl)pyridine-2-sulphonamide trifluoroacetate.

A mixture of this material, (R)-7-trifluoromethyl-1,4-benzodioxan-2-ylmethyl 4-toluenesulphonate (1.0 g), potassium carbonate (3.6 g), and potassium iodide (10 mg) in acetonitrile (130 ml) was heated at reflux, with stirring, under nitrogen for 24 hours. The reaction was cooled, filtered and concentrated under reduced pressure to afford a brown viscous oil. Purification was effected by flash chromatography on silica gel eluting with a 95:5 mixture of dichloromethane and methanol. The appropriate fractions were combined and the solvent removed under reduced pressure to give a yellow oil (1.0 g) which contained some impurities. The oil was dissolved in ethyl acetate (100 ml) and the solution extracted with dilute hydrochloric acid (5 M; 3×300 ml). The aqueous phase was basified to pH 14 by the addition of dilute aqueous sodium hydroxide solution (5 M) and the product was extracted into ethyl acetate (3×100 ml). The organic extracts were combined, dried over anhydrous magnesium sulphate and evaporated to dryness to give a clear oil that was triturated with diethyl ether (10 ml) to afford (S)-(−)-N-J[1-(7-trifluoromethyl-1,4-benzodioxan-2-ylmethyl)-4-piperidyl]methyl,pyridine-2-sulphonamide (0.22 g) m.p. 138–140 ° C., $[\alpha]_D^{21}$ −44.7° (c=0.483, MeOH).

EXAMPLE 13

A mixture of (R)-7-bromo-1,4-benzodioxan-2-ylmethyl 4-toluenesulphonate (6.5 g, prepared as described in WO97/03071), N-benzylidene-4-piperidylmethylamine (3.0 g), potassium carbonate (4.1 g), and potassium iodide (10 mg) in acetonitrile (200 ml) was heated at reflux, with stirring, under nitrogen for 24 hours. The reaction was cooled, filtered and concentrated under reduced pressure to afford (S)-N-benzylidene-1-[1-(7-bromo-1,4-benzodioxan-2-ylmethyl)-4-piperidyl]methylamine (6.3 g) as an orange-brown viscous oil.

The crude product from the previous reaction (6.3 g) was stirred in aqueous potassium hydrogen sulphate solution (0.6 M; 125 ml) for three hours at ambient temperature. The solution was washed with ether (3×200 ml), basified using aqueous sodium hydroxide solution (5 M) then extracted with ether (3×200 ml). The combined ethereal layers were washed with water (200 ml), dried over magnesium sulphate and evaporated to dryness to afford (S)-4-(aminomethyl)-1-(7-bromo-1,4-benzodioxan-2-ylmethyl)piperidine (4.0 g) as a brown oil.

Triethylamine (0.63 ml) was added to a solution of (S)-4-(aminomethyl)-1-(7-bromo-1,4-benzodioxan-2-ylmethyl)piperidine (0.5 g) and 2,3-dichlorobenzenesulphonyl chloride (0.74 g) in dichloromethane (15 ml) and stirred under nitrogen for 24 hours. The reaction was diluted with dichloromethane (100 ml), washed with water (100 ml) and brine (100 ml), dried over anhydrous magnesium sulphate and concentrated under reduced pressure. Purification by flash chromatography on silica gel eluting with a 9:1 mixture of dichloromethane and methanol gave (S)-(−)-N-{[1-(7-bromo-1,4-benzodioxan-2-ylmethyl)-4-piperidyl]methyl}-2,3-dichlorobenzensulphonamide as a cream solid (0.8 g) m.p. 93-95° C., $[\alpha]_D^{22}$ −37.1°(c=0.93, MeOH).

EXAMPLE 14

Hexamethylenetetramine (47.5 g) was added portionwise to a stirred solution of 4-trifluoromethylphenol (50 g) in trifluoroacetic acid (680 ml) and the mixture was heated at reflux temperature for 24 hours. After cooling, water (355 ml) was added followed by aqueous sulphuric acid (50% v/v, 190 ml) and the reaction was stirred at ambient temperature for 4 hours. The acidic aqueous phase was extracted with diethyl ether (3×500 ml). The combined organic extracts were washed with hydrochloric acid (5M, 3×500 ml) then water (500 ml) and dried over magnesium sulphate. The solvent was removed under reduced pressure and the residue purified by column chromatography on silica eluting with a 4:1 mixture of petroleum ether (b.p. 40–60° C.) and ethyl acetate. The appropriate fractions were combined and the solvent removed under reduced pressure to give 5-trifluoromethyl-2-hydroxybenzaldehyde (25 g) as a light pink solid.

A mixture of (R)-glycidyl 4-toluenesulphonate (24 g), 5-trifluoromethyl-2-hydroxybenzaldehyde (20 g) and potassium carbonate (16 g) in dimethylformamide (550 ml) was stirred and heated at 60° C. for 72 hours. After cooling, brine (1.5 L) was added and the resultant mixture extracted with ether (4×500 ml). The combined ether extracts were washed with brine (2×500 ml), then water (500 ml) and dried over magnesium sulphate. The residue was purified by flash column chromatography on silica eluting with a 3:1 mixture of petroleum ether (b.p. 40–60 ° C.) and ethyl acetate to give (R)-5-trifluoromethyl-2-(2,3-epoxypropoxy)benzaldehyde (18.7 g) as a yellow oil.

A mixture of the product from the previous reaction (18.7 g) and 3-chloroperoxybenzoic acid (57–86%, 48.7 g) in dichloromethane (1L) was heated under reflux for 24 hours then allowed to cool to ambient temperature. The mixture was washed with saturated aqueous sodium bicarbonate (3×700 ml), water (2×700 ml) and brine (700 ml), then dried over magnesium sulphate. The solvent was evaporated to give crude (R)-5-trifluoromethyl-2-(2,3-epoxypropoxy) phenyl formate (16.7 g).

A mixture of the product from the previous reaction (16.7 g), tetrahydrofuran (220 ml) and a saturated aqueous potassium carbonate solution (175 ml) was stirred vigorously at ambient temperature for 24 hours. Water (500 ml) was added and the organic phase was removed. The aqueous phase was extracted with ethyl acetate (3×300 ml) and the combined organic extracts were dried over magnesium sulphate. The solvent was removed under reduced pressure and the residue purified by flash column chromatography on silica eluting with a 4:1 grading to 1:1 mixture of petroleum ether (b.p. 40–60° C.) and ethyl acetate. Appropriate fractions were combined and the solvent was removed under reduced pressure to give (S)-7-trifluoromethyl-1,4-benzodioxan-2-ylmethanol (12 g) as a yellow oil.

A solution of 4-toluenesulphonyl chloride (9.6 g) in dichloromethane (60 ml) was added dropwise to a solution the product from the previous reaction (10.7 g) and 4-dimethylaminopyridine (6.7 g) in dichloromethane (90 ml) between 0–5° C.

The mixture was stirred at ambient temperature for 4 hours then allowed to stand for 18 hours. The solution was washed with dilute hydrochloric acid (5M, 2×300 ml) dried over magnesium sulphate and the solvent was removed under reduced pressure to afford (R)-7-trifluoromethyl-1,4-benzodioxan-2-ylmethyl 4-toluenesulphonate (15.5 g) as a white solid.

A mixture of the product from the previous reaction (2 g), N-benzylidene-4-piperidylmethylamine (1 g), potassium carbonate (1.35 g), and potassium iodide (10 mg) in acetonitrile (75 ml) was heated at reflux, with stirring, under nitrogen for 24 hours. The reaction was cooled, filtered and concentrated under reduced pressure to afford (S)-N-benzylidene-1-[1-(7-trifluoromethyl-1,4-benzodioxan-2-ylmethyl)-4-piperidyl]methylamine (6.3 g) as a yellow viscous oil.

The crude product from the previous reaction was stirred in aqueous potassium hydrogen sulphate solution (0.6 M; 36 ml) for 5 hours at ambient temperature then left to stand for 18 hours. The solution was washed with ether (2×50 ml), basified using aqueous sodium hydroxide solution (5 M) then extracted with ether (3×100 ml). The combined ethereal layers were dried over magnesium sulphate and evaporated to dryness to afford (S)-4-(aminomethyl)-1-(7-trifluoromethyl-1,4-benzodioxan-2-ylmethyl)piperidine (0.87 g) as an orange oil.

A mixture of the product from the previous reaction (0.87 g), 2,3-dichlorobenzenesulphonyl chloride (1.29 g), triethylamine (1.1 ml) and dichloromethane (40 ml) was stirred under nitrogen for 3 hours then left to stand for 18 hours. The solvent was removed under reduced pressure and the residue was purified by flash chromatography on silica gel eluting with a 40:1 mixture of dichloromethane and methanol to give (S)-(−)-2,3-dichloro-N-{[1-(7-trifluoromethyl-1,4-benzodioxan-2-ylmethyl)-4-piperidyl]methyl}benzenesulphonamide as a cream solid (0.72 g), m.p. 139–140° C., $[\alpha]_D^{22}$ −36.7°(c=0.18, MeOH).

EXAMPLES 15–39
General Procedure

Triethylamine (0.042 ml, 0.3 mmol) was added to a 2 ml screw-top vial containing a stock solution of (S)-4-(aminomethyl)-1-(7-chloro-1,4-benzodioxan-2-ylmethyl) piperidine in dichloromethane (0.1M, 1 ml, 0.1 mmol) and an arylsulphonyl chloride (0.2 mmol). The reaction vials were sealed with a screw-cap then stirred at ambient temperature for 66 hours. The cap was removed and the solvent was removed initially under a stream of nitrogen, then under reduced pressure at 40° C. The residues were redissolved in dichloromethane (1 ml) and an aliquot (0.020 ml) removed and added to digol (2 ml). The digol solution was shaken until homogeneous and the mixture analysed in in vitro biological assays.

Each of the following compounds was prepared, by selecting the appropriate arylsulphonyl chloride, as a crude sample using the general procedure detailed above:

EXAMPLE 15

(S)-N-{[1-(7-Chloro-1,4-benzodioxan-2-ylmethyl)-4-piperidyl]methyl}-2,4-dinitrobenzenesulphonamide

EXAMPLE 16

(S)-N-{[1-(7-Chloro-1,4-benzodioxan-2-ylmethyl)-4-piperidyl]methyl}-2,5-bis(2,2,2-trifluoroethoxy)benzenesulphonamide

EXAMPLE 17

(S)-2-Chloro-N-{[1-(7-chloro-1,4-benzodioxan-2-ylmethyl)-4-piperidyl]methyl}-4-trifluoromethylbenzenesulphonamide

EXAMPLE 18

(S)-N-{[1-(7-Chloro-1,4-benzodioxan-2-ylmethyl)-4-piperidyl]methyl}-4-iodo-benzenesulphonamide

EXAMPLE 19

(S)-N-{[1-(7-Chloro-1,4-benzodioxan-2-ylmethyl)-4-piperidyl]methyl}-4-methoxy-2,3,6-trimethylbenzenesulphonamide

EXAMPLE 20

(S)-N-{[1-(7-Chloro-1,4-benzodioxan-2-ylmethyl)-4-piperidyl]methyl}naphth[2,1-d][1,2,3]oxadiazole-5-sulphonamide

EXAMPLE 21

(S)-N-{[1-(7-Chloro-1,4-benzodioxan-2-ylmethyl)-4-piperidyl]methyl}-2,4,6-trimethylbenzenesulphonamide

EXAMPLE 22

(S)-N-{[1-(7-Chloro-1,4-benzodioxan-2-ylmethyl)-4-piperidyl]methyl}-2,3,4,5,6-pentamethylbenzenesulphonamide

EXAMPLE 23

(S)-N-{[1-(7-Chloro-1,4-benzodioxan-2-ylmethyl)-4-piperidyl]methyl}-5-(diethylamino)naphthalene-1-sulphonamide

EXAMPLE 24

(S)-N-{[1-(7-Chloro-1,4-benzodioxan-2-ylmethyl)-4-piperidyl]methyl}-4-trifluoromethylbenzenesulphonamide

EXAMPLE 25

(S)-N-{[1-(7-Chloro-1,4-benzodioxan-2-ylmethyl)-4-piperidyl]methyl}-3-nitrobenzenesulphonamide

EXAMPLE 26

(S)-N-{[1-(7-Chloro-1,4-benzodioxan-2-ylmethyl)-4-piperidyl]methyl}-4-methyl-3,5-dinitrobenzenesulphonamide

EXAMPLE 27

(S)-5-Chloro-N-{[1-(7-chloro-1,4-benzodioxan-2-ylmethyl)-4-piperidyl]methyl}-2-methoxybenzenesulphonamide

EXAMPLE 28

(S)-N-{[1-(7-Chloro-1,4-benzodioxan-2-ylmethyl)-4-piperidyl]methyl}-3-trifluoromethylbenzenesulphonamide

EXAMPLE 29

(S)-N-{[1-(7-Chloro-1,4-benzodioxan-2-ylmethyl)-4-piperidyl]methyl}-4-trifluoromethoxybenzenesulphonamide

EXAMPLE 30

(S)-N-{[1-(7-Chloro-1,4-benzodioxan-2-ylmethyl)-4-piperidyl]methyl}-2-naphthalenesulphonamide

EXAMPLE 31

(S)-N-{[1-(7-Chloro-1,4-benzodioxan-2-ylmethyl)-4-piperidyl]methyl}-1-naphthalenesulphonamide

EXAMPLE 32

(S)-N-{[1-(7-Chloro-1,4-benzodioxan-2-ylmethyl)-4-piperidyl]methyl}-2,5-dimethoxybenzenesulphonamide

EXAMPLE 33

(S)-N-{[1-(7-Chloro-1,4-benzodioxan-2-ylmethyl)-4-piperidyl]methyl}-4-methylbenzenesulphonamide

EXAMPLE 34

(S)-N-{[1-(7-Chloro-1,4-benzodioxan-2-ylmethyl)-4-piperidyl]methyl}benzene-sulphonamide

EXAMPLE 35

(S)-N-{[1-(7-Chloro-1,4-benzodioxan-2-ylmethyl)-4-piperidyl]methyl}-5-fluoro-2-methylbenzenesulphonamide

EXAMPLE 36

(S)-2,5-Dibromo-N-{[1-(7-Chloro-1,4-benzodioxan-2-ylmethyl)-4-piperidyl]methyl}-benzenesulphonamide

EXAMPLE 37

(S)-N-{[1-(7-Chloro-1,4-benzodioxan-2-ylmethyl)-4-piperidyl]methyl}-2-nitro-benzenesulphonamide

EXAMPLE 38

(S)-N-{[1-(7-Chloro-1,4-benzodioxan-2-ylmethyl)-4-piperidyl]methyl}-2,3,4-trifluorobenzenesulphonamide

EXAMPLE 39

(S)-2,5-Dibromo-N-{[1-(7-chloro-1,4-benzodioxan-2-ylmethyl)-4-piperidyl]methyl}-3,6-difluorobenzenesulphonamide.

EXAMPLES 40–49

General Procedure

Stock solutions of the appropriate starting amine of formula XVI in dichloromethane (0.1 M, 0.3–0.8 ml, 0.03–0.08 mmol) and triethylamine in dichloromethane (50% v/v, 3 equivalents) were added to a number of 2 ml screw-top vials, each containing a different aryl sulphonyl chloride (2 equivalents). This process was repeated for each of the 3 different amines. The reaction vials were sealed then agitated on an orbital shaker at ambient temperature for 14 hours. The caps were removed and the solvent was allowed to evaporate under ambient conditions, then under reduced pressure at 40° C. The residues were redissolved in dichloromethane to a standard concentration of 0.1 M then further diluted to $10^{-3}$ M with digol. The digol solution was shaken until homogeneous and the mixture containing the active compound analysed in the in vitro biological assays.

The following compounds were prepared in a single batch, as the major component in a mixture (purities indicated).

Examples 40–43 used (S)-4-(aminomethyl)-1-(7-chloro-1,4-benzodioxan-2-ylmethyl)piperidine, prepared as described in example 1 of WO97/03071, as the starting amine:

EXAMPLE 40

(S)-(−)-N-{[1-(7-Chloro-1,4-benzodioxan-2-yl methyl)-4-piperidyl]methyl}-2-fluorobenzenesulphonamide, HPLC 56% (3.03 min); m/z 455 (MH$^+$).

EXAMPLE 41

(S)-(−)-2-Chloro-N-{[1-(7-chloro-1,4-benzodioxan-2-ylmethyl)-4-piperidyl] methyl}benzenesutphonamide, HPLC 73% (3.14 min); m/z 471 (MH$^+$).

EXAMPLE 42

(S)-(−)-3-Chloro-N-{[1-(7-chloro-1,4-benzodioxan-2-ylmethyl)-4-piperidyl]methyl}-4-fluoro-benzenesulphonamide, HPLC 62% (3.35 min); m/z 489 (MH+).

EXAMPLE 43

(S)-(−)-2,3-Dichloro-N-{[1-(7-chloro-1,4-benzodioxan-2-ylmethyl)-4-piperidyl] methyl}benzenesulphonamide, HPLC 66% (3.39 min); m/z 505 (MH$^+$).

Examples 43–47 used (S)-4-(aminomethyl)-1-(7-bromo-1,4-benzodioxan-2-ylmethyl)piperidine, prepared as in example 13 as the starting amine:

EXAMPLE 44

(S)-(−)-4-Acetamido-N-{[1-(7-bromo-1,4-benzodioxan-2-ylmethyl}-4-piperidyl]methyl) benzenesulphonamide, HPLC 76% (2.74 min); m/z 538, 540 (MH⁺).

EXAMPLE 45

(S)-(−)-N-{[1-(7-Bromo-1,4-benzodioxan-2-ylmethyl)-4-piperidyl]methyl}-2-fluorobenzenesulphonamide, HPLC 50% (3.04 min); m/z 499, 501 (MH⁺).

EXAMPLE 46

(S)-(−)-N-{[1-(7-Bromo-1,4-benzodioxan-2-ylmethyl)-4-piperidyl]methyl}-2-chlorobenzenesulphonamide, HPLC 83% (3.18 min); m/z 515, 517 (MH⁺).

EXAMPLE 47

(S)-(−)-N-{[1-(7-Bromo-1,4-benzodioxan-2-ylmethyl)-4-piperidyl]methyl}-2,4-difluorobenzenesulphonamide, HPLC 88% (3.14 min); m/z 517, 519 (MH⁺).

EXAMPLE 48

(S)-(−)-3-Chloro-N-{[1-(7-bromo-1,4-benzodioxan-2-ylmethyl)-4-piperidyl]methyl}-4-fluorobenzenesulphonamide, HPLC 74% (3.39 min); m/z 533, 535, (MH⁺).

EXAMPLE 49

(S)-(−)-2,3-Dichloro-N-{[1-($^6$,$^7$-methylenedioxy-1,4-benzodioxan-2-ylmethyl)-4-piperidyl] methyl}benzenesulphonamide, HPLC 71% (3.07 min); m/z 515 (MH⁺).

Example 49 used (S)-$^4$-(aminomethyl)-1-(6,7-methylenedioxy-1,4-benzodioxan-2-ylmethyl)piperidine, prepared as described below, as the starting amine.

A mixture of (R)-6,7-methylenedioxy-1,4-benzodioxan-2-ylmethyl 4-toluenesulphonate (2.0 g), N-benzylidene-4-piperidylmethylamine(1.11 g), potassium carbonate (3.8 g), and potassium iodide (100 mg) in acetonitrile (50 ml) was heated at reflux, with stirring, under nitrogen for 24 hours. The reaction was cooled, filtered and concentrated under reduced pressure to afford (S)-N-benzylidene-1-[1-(7-bromo-1,4-benzodioxan-2-ylmethyl)-4-piperidyl] methylamine (6.3 g) as a gum.

The crude product from the previous reaction (6.3 g) was stirred in aqueous potassium hydrogen sulphate solution (1 M; 100 ml) for 14 hours at ambient temperature. The solution was washed with ether (3×200 ml), basified using aqueous sodium hydroxide solution (5 M) then extracted with dichloromethane (3×100 ml). The combined extracts were washed with water (200 ml), dried over magnesium sulphate and evaporated to dryness to afford (S)-$^4$-(aminomethyl)-1-6,7-methylenedioxy-1,4-benzodioxan-2-ylmethyl)piperidine (1.18 g), $[\alpha]_D^{23}$ −63.4° (c=0.4, MeOH). as a viscous oil.

Analytical conditions for examples 40 to 49 are as follows:

HPLC conditions—Peco C18 column, 3cm×3mm i.d.; 100% aqueous ammonium acetate (0.1 M), adjusted to pH 4.55 with acetic acid, to 100% acetonitrile linear gradient in 5 minutes, 2 ml/min; wavelength detection band 250–320nm, 5 min detection time. Percent purity was determined by integration of detectable peak areas.

Mass Spectrometric conditions—Atmospheric pressure chemical ionisation, 150–500 Da mass detection range.

EXAMPLE 50

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose or part of a unit dose of active compound.

b) Tablets

Tablets are prepared from the following ingredients.

|  | Parts by weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinyl-pyrrolidone in ethanol. The dry granulate is blended with the magnesium stearate and the rest of the starch. The mixture is then compressed in a tabletting machine to give tablets each containing a unit dose or a part of a unit dose of active compound.

Enteric Coated Tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

What is claimed is:

1. Compounds of formula I

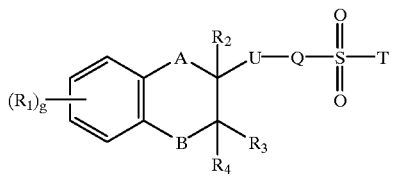

I including enantiomers and pharmaceutically acceptable salts thereof in which both A and B are —O—;

g is 0, 1, 2, 3 or 4;

$R_1$ represents an alkyl group containing 1 to 3 carbon atoms optionally substituted by one or more halo; an alkoxy group containing 1 to 3 carbon atoms optionally substituted by one or more halo; halo; 6,7-methylenedioxy optionally C-substituted by one or two alkyl groups containing 1 to 3 carbon atoms; or an alkylthio group containing 1 to 3 carbon atoms optionally substituted by one or more halo; the substituents represented by $R_1$ being the same or different when g is 2, 3 or 4;

$R_2$ is H, an alkyl group containing 1 to 3 carbon atoms, or an alkoxy group containing 1 to 3 carbon atoms;

$R_3$ and $R_4$, which are the same or different, are H, or an alkyl group containing 1 to 3 carbon atoms;

U is an alkylene chain containing 1 to 3 carbon atoms, optionally substituted by one or more alkyl groups each containing 1 to 3 carbon atoms;

Q represents a divalent group of formula IIc

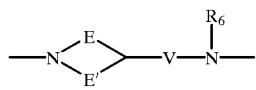

IIc in which E and E' are both ethylene, V is methylene, and $R_6$ is H

T represents phenyl, 1- or 2-naphthyl, 5-naphth[2,1-d][1,2,3]oxadiazolyl, 2-, 3- or 4-pyridyl, 2-, 4- or 5-pyrimidinyl, 2- or 3-thienyl, 2- or 3-furyl, 2-, 3- or 7-benzo[b]furanyl, 2,3-dihydro-7-benzo[b]furanyl, 2-, 3- or 7-benzo[b]thiophenyl, 3-, 4- or 5-pyrazolyl, 1,2,3-triazol-4-yl, 1,2,3-triazol-5-yl, 1,2,4-triazol-2-yl, 5-tetrazolyl, 2-,3- or quinolinyl, 2- or 4-quinazolinyl, 3-, 4- or 5-isoxazolyl, 2-, 4- or 5-oxazolyl, 3-, 4- or 5-isothiazolyl or 2-, 4- or 5-thiazolyl each of which may be optionally substituted by one or more substituents selected from a) halo, b) an alkyl group containing 1 to 4 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) hydroxy, f) an acyloxy group containing 1 to 3 carbon atoms, g) hydroxymethyl, h) cyano, i) an alkanoyl group containing 1 to 6 carbon atoms, j) an alkoxycarbonyl group containing 2 to 6 carbon atoms, k) a carbamoyl group or carbamoylmethyl group each optionally N-substituted by one or two alkyl groups each containing 1 to 3 carbon atoms, I)a sulphamoyl or sulphamoylmethyl group each optionally N-substituted by one or two alkyl groups each containing 1 to 3 carbon atoms, m) an amino group optionally substituted by one or two alkyl groups each containing 1 to 5 carbon atoms, n) 1-pyrrolidinyl or 1-piperidinyl, o) nitro or p) acetamido.

2. Compounds of formula I, as claimed in claim 1, in which A is —O—, B is —O—, g is 1, $R_1$ is preferably halo or an alkyl group containing 1 to 3 carbon atoms optionally substituted by one or more halo, $R_2$ is H, $R_3$ and $R_4$ are both H, U is methylene, Q is a group of formula IIc in which E and E' are both ethylene, V is methylene, $R_6$ is H, and T is 1-naphthyl, 2-naphthyl, 5-naphth[2,1-d][1,2,3]oxadiazolyl, 2-pyridyl, 3-pyridyl, phenyl, 4-methylphenyl, 2,4,6-trimethylphenyl, 2,3,4,5,6-pentamethylphenyl, 2-fluorophenyl, 4-fluorophenyl, 2,6-difluorophenyl, 2,4-difluorophenyl, 2,3,4-trifluorophenyl, 2-chlorophenyl, 4-chlorophenyl, 2,5-dibromophenyl, 4-iodophenyl, 2,5-dibromo-3,6-difluorophenyl, 4-methoxyphenyl, 2,5-dimethoxyphenyl, 3,4-dimethoxyphenyl, 4-methoxy-2,3,6-trimethylphenyl, 5-chloro-2-methoxyphenyl, 5-fluoro-2-methylphenyl, 4-trifluoromethoxyphenyl, 2,5-bis(2,2,2-trifluoroethoxy)phenyl, 3-trifluoromethylphenyl, 4-trifluoromethylphenyl, 2-chloro-4-trifluoromethylphenyl, 4-acetamidophenyl, 2-nitrophenyl, 3-nitrophenyl, 4-nitrophenyl, 2,4-dinitrophenyl, 4-methyl-3,5-dinitrophenyl, 5-(diethylamino)-1-naphthyl, 2,3-dichlorophenyl or 3-chloro-4-fluorophenyl.

3. Compounds of formula I, as claimed in claim 1, selected from:
N-{[1-(7-chloro-1,4-benzodioxan-2-ylmethyl)-4-piperidyl]methyl}pyridine-2-sulphonamide;
N-{[1-(7-chloro-1,4-benzodioxan-2-ylmethyl)-4-piperidyl]methyl}pyridine-3-sulphonamide;
N-{[1-(7-chloro-1,4-benzodioxan-2-ylmethyl)-4-piperidyl]methyl}-4-nitrobenzenesulphonamide;
N-{[1-(7-chloro-1,4-benzodioxan-2-ylmethyl)-4-piperidyl]methyl}-4-fluorobenzenesulphonamide;
N-{[1-(7-chloro-1,4-benzodioxan-2-ylmethyl)-4-piperidyl]methyl}-3,4-dimethoxybenzenesulphonamide;
N-{[1-(7-chloro-1,4-benzodioxan-2-ylmethyl)-4-piperidyl]methyl}-2,4-difluorobenzenesulphonamide;
4-acetamido-N-{[1-(7-chloro-1,4-benzodioxan-2-ylmethyl)-4-piperidyl]methyl}-benzenesulphonamide;
N-{[1-(7-chloro-1,4-benzodioxan-2-ylmethyl)-4-piperidyl]methyl}-4-methoxybenzenesulphonamide;
N-{[1-(7-chloro-1,4-benzodioxan-2-ylmethyl)-4-piperidyl]methyl}-2,6-difluorobenzenesulphonamide;
N-{[1-(7-chloro-1,4-benzodioxan-2-ylmethyl)-4-piperidyl]methyl}-4-chlorobenzenesulphonamide;
N-{[1-(7-trifluoromethyl-1,4-benzodioxan-2-ylmethyl)-4-piperidyl]methyl}pyridine-2-sulphonamide
N-{[1-(7-bromo-1,4-benzodioxan-2-ylmethyl)-4-piperidyl]methyl}-2,3-dichlorobenzensulphonamide
2,3-dichloro-N-{[1-(7-trifluoromethyl-1,4-benzodioxan-2-ylmethyl)-4-piperidyl]methyl}benzenesulphonamide
N-{[1-(7-chloro-1,4-benzodioxan-2-ylmethyl)-4-piperidyl]methyl}-2,4-dinitrobenzenesulphonamide
N-{[1-(7-chloro-1,4-benzodioxan-2-ylmethyl)-4-piperidyl]methyl}-2,5-bis(2,2,2-trifluoroethoxy)benzenesulphonamide
2-chloro-N-{[1-(7-chloro-1,4-benzodioxan-2-ylmethyl)-4-piperidyl]methyl}-4-trifluoromethylbenzenesulphonamide
N-{[1-(7-chloro-1,4-benzodioxan-2-ylmethyl)-4-piperidyl]methyl}-2,4-dinitrobenzenesulphonamide;
N-{[1-(7-chloro-1,4-benzodioxan-2-ylmethyl)-4-piperidyl]methyl}2,5-bis(2,2,2-trifluoroethoxy)benzenesulphonamide;
2-chloro-N-{[1-(7-chloro-,4-benzodioxan-2-ylmethyl)-4-piperidyl]methyl}-4-trifluoromethylbenzenesulphonamide;
N-{[1-(7-chloro-1,4-benzodioxan-2-ylmethyl)-4-piperidyl]methyl}-4-iodobenzenesulphonamide;
N-{[1-(7-chloro-1,4-benzodioxan-2-ylmethyl)-4-piperidyl]methyl}-4-methoxy-2,3,6-trimethylbenzenesulphonamide;
N-{[1-(7-chloro-1,4-benzodioxan-2-ylmethyl)-4-piperidyl]methyl}naphth[2,1-d][1,2,3]-oxadiazole-5-sulphonamide;
N-{[1-(7-chloro-1,4-benzodioxan-2-ylmethyl)-4-piperidyl]methyl}-2,4,6-trimethylbenzenesulphonamide;
N-{[1-(7-chloro-1,4-benzodioxan-2-ylmethyl)-4-piperidyl]methyl}-2,3,4,5,6-pentamethylbenzenesulphonamide;
N-{[1-(7-chloro-1,4-benzodioxan-2-ylmethyl)-4-piperidyl]methyl}-5-(diethylamino)naphthalene-1-sulphonamide;
N-{[1-(7-chloro-1,4-benzodioxan-2-ylmethyl)-4-piperidyl]methyl}-4-trifluoromethylbenzenesulphonamide;

N-{[1-(7-chloro-1,4-benzodioxan-2-ylmethyl)-4-piperidyl]methyl}-3-nitrobenzenesulphonamide;
N-{[1-(7-chloro-1,4-benzodioxan-2-ylmethyl)-4-piperidyl]methyl}-4-methyl-3,5-dinitrobenzenesulphonamide;
5-chloro-N-{[1-(7-chloro-1,4-benzodioxan-2-ylmethyl)-4-piperidyl]methyl}-2-methoxybenzenesulphonamide;
N-{[1-(7-chloro-1,4-benzodioxan-2-ylmethyl)-4-piperidyl]methyl}-3-trifluoromethylbenzenesulphonamide;
N-{[1-(7-chloro-1,4-benzodioxan-2-ylmethyl)-4-piperidyl]methyl}-4-trifluoromethoxybenzenesulphonamide;
N-{[1-(7-chloro-1,4-benzodioxan-2-ylmethyl)-4-piperidyl]methyl}-2-naphthalenesulphonamide;
N-{[1-(7-chloro-1,4-benzodioxan-2-ylmethyl)-4-piperidyl]methyl}-1-naphthalenesulphonamide;
N-{[1-(7-chloro-1,4-benzodioxan-2-ylmethyl)-4-piperidyl]methyl}-2,5-dimethoxybenzenesulphonamide;
N-{[1-(7-chloro-1,4-benzodioxan-2-ylmethyl)-4-piperidyl]methyl}-4-methylbenzenesulphonamide;
N-{[1-(7-chloro-1,4-benzodioxan-2-ylmethyl)-4-piperidyl]methyl}benzenesulphonamide;
N-{[1-(7-chloro-1,4-benzodioxan-2-ylmethyl)-4-piperidyl]methyl}-5-fluoro-2-methylbenzenesulphonamide;
2,5-dibromo-N-{[1-(7-chloro-1,4-benzodioxan-2-ylmethyl)-4-piperidyl]methyl}-benzenesulphonamide;
N-{[1-(7-chloro-1,4-benzodioxan-2-ylmethyl)-4-piperidyl]methyl}-2-nitrobenzenesulphonamide;
N-{[1-(7-chloro-1,4-benzodioxan-2-ylmethyl)-4-piperidyl]methyl}-2,3,4-trifluorobenzenesulphonamide;
2,5-dibromo-N-{[1-(7-chloro-1,4-benzodioxan-2-ylmethyl)-4-piperidyl]methyl}-3,6-difluorobenzenesulphonamide;
N-{[1-(7-chloro-1,4-benzodioxan-2-ylmethyl)-4-piperidyl]methyl}-2-fluorobenzenesulphonamide;
2-chloro-N-{[1-(7-chloro-1,4-benzodioxan-2-ylmethyl)-4-piperidyl]methyl}-benzenesulphonamide;
3-chloro-N-{[1-(7-chloro-1,4-benzodioxan-2-ylmethyl)-4-piperidyl]methyl}-4-fluorobenzenesulphonamide;
2,3-dichloro-N-{[1-(7-chloro-1,4-benzodioxan-2-ylmethyl)-4-piperidyl]methyl}benzenesulphonamide;
4-acetamido-N-{[1-(7-bromo-1,4-benzodioxan-2-ylmethyl)-4-piperidyl]methyl}-benzenesulphonamide;
N-{[1-(7-bromo-1,4-benzodioxan-2-ylmethyl)-4-piperidyl]methyl}-2-fluorobenzenesulphonamide;
N-{[1-(7-bromo-1,4-benzodioxan-2-ylmethyl)-4-piperidyl]methyl}-2-chlorobenzenesulphonamide;
N-{[1-(7-bromo-1,4-benzodioxan-2-ylmethyl)-4-piperidyl]methyl}-2,4-difluorobenzenesulphonamide;
3-chloro-N-{[1-(7-bromo-1,4-benzodioxan-2-ylmethyl)-4-piperidyl]methyl}-4-fluorobenzenesulphonamide;
2,3-dichloro-N-{[1-(6,7-methylenedioxy-1,4-benzodioxan-2-ylmethyl)-4-piperidyl]methyl}benzenesulphonamide;
and pharmaceutically acceptable salts thereof in the form of individual enantiomers, racemates, or other mixtures of enantiomers.

4. A method of treating depression, anxiety, psychoses, tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, or spasticity in human beings, which comprises the administration of a therapeutically effective amount of a compound of formula I, as claimed in claim 1, to a patient in need thereof.

5. A process for the preparation of compounds of formula I in which Q is a group of formula IIc, comprising the reaction of a compound of formula XIV

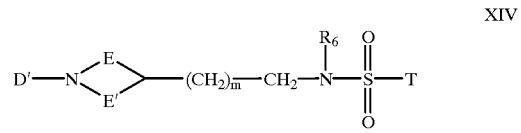

XIV in which D' is H and m is 0, 1 or 2, with a compound of formula IV

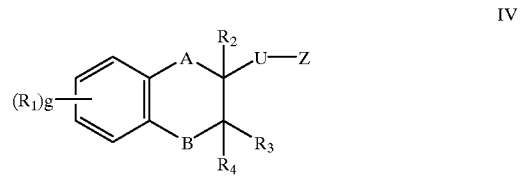

IV in which Z is a leaving group, optionally in the presence of a base, optionally in the presence of a presence of a suitable solvent, and optionally in the presence of a catalyst.

6. A pharmaceutical composition comprising a compound of formula I, as claimed in claim 1 in conjunction with a pharmaceutically acceptable diluent or carrier.

* * * * *

UNITED STATES PATENT AND TRADEMARK OFFICE
CERTIFICATE OF CORRECTION

PATENT NO.: 6,136,825

DATED: October 24, 2000

INVENTOR(S): WISHART et al.

It is certified that error appears in the above-identified patent and that said Letters Patent is hereby corrected as shown below:

In the Abstract, line 10, insert "sexual" before "dysfunction".

Col. 29, claim 1, line 47, "I a" should be --l) a--.

Signed and Sealed this

Eighth Day of May, 2001

*Attest:*

NICHOLAS P. GODICI

*Attesting Officer*      *Acting Director of the United States Patent and Trademark Office*